United States Patent [19]

Rieke et al.

[11] Patent Number: 4,933,164

[45] Date of Patent: Jun. 12, 1990

[54] STABILIZERS FOR STAINING SOLUTIONS

[75] Inventors: Erwin Rieke, Seeheim; Renate Kaschek, Reinheim, both of Fed. Rep. of Germany

[73] Assignee: Merck Patent Gesellschaft mit beschränkter Haftung, Darmstadt, Fed. Rep. of Germany

[21] Appl. No.: 263,318

[22] Filed: Oct. 27, 1988

[30] Foreign Application Priority Data

Oct. 28, 1987 [DE] Fed. Rep. of Germany ....... 3736490

[51] Int. Cl.⁵ .................................................. G01N 1/00
[52] U.S. Cl. ........................................ 424/3; 514/970; 514/971
[58] Field of Search ............................................ 424/3

[56] References Cited

U.S. PATENT DOCUMENTS

| | | | |
|---|---|---|---|
| 4,392,864 | 7/1983 | Helfrich | 424/3 |
| 4,687,489 | 4/1987 | Ricke et al. | 424/3 |
| 4,741,898 | 5/1988 | Mallik et al. | 424/3 |

*Primary Examiner*—Douglas W. Robinson
*Assistant Examiner*—Raymond J. Henley, III
*Attorney, Agent, or Firm*—Millen, White & Zelano

[57] ABSTRACT

Stabilized staining solutions are provided which comprise dyes and a combination of dimethylammonium sulfate and crystallization inhibitors. The staining solutions are used for staining in hematology, cytology and histology.

12 Claims, No Drawings

STABILIZERS FOR STAINING SOLUTIONS

BACKGROUND OF THE INVENTION

The invention relates to the stabilization of blood-staining solutions, especially those which contain thiazine dyes.

Differential blood counts have been performed for a long time by means of the known staining solutions according to Giemsa, May-Grunwald, Leishman and Wright. An important disadvantage of these staining solutions is that the investigation results from various laboratories cannot be compared with one another because of the different quality of the commercially available dyes (J. Clin. Path. 28, 680 (1975)). There are not only large differences in quality between the dyes from various manufacturers, but the dyes are also subject to chemical changes over time. Because of the instability of, in particular, the methylene blue molecule which especially in an alkaline medium, is converted by oxidative demethylation into the next-lower homologues azure A, azure B, azure C and thionin, the said staining solutions cannot be produced with constant quality and can therefore also not be standardized. Essentially, the staining properties change due to a decrease in the optical density of the thiazine components, which is determined at about 645 nm. As a result, there is a continuous shift in the blue/red color ratio and, after some time, this leads to stainings which are no longer acceptable. Moreover, preservation of the reproducible staining properties is made more difficult by the fact that the dyes in the staining solutions tend, especially at low temperatures, to crystallize out of solution, with eosin crystallizing out at a higher rate than the thiazine components. Standardization of the staining reactions, which is indispensable in this field because of increasing automation, is virtually impossible with the known blood-staining solutions.

It is already known from German Offenlegungsschrift 3,533,515 that the stability of staining solutions can be greatly increased by an addition of dimethylammonium sulfate. Whereas unstabilized solutions, depending on the quality of the raw materials employed, tend to suffer precipitations of dye crystals sometimes even at room temperature, but in most cases at lower temperatures, the staining solutions stabilized with dimethylammonium sulfate remain clear, for example at room temperature, but a formation of precipitates occurs in some cases in the temperature region around 9° C., with a resulting deterioration in the staining quality.

SUMMARY OF THE INVENTION

The invention is based on the object of providing stabilizers for staining solutions, which guarantee a long shelf life and prevent the precipitation of dyes at low temperatures, give generally comparable results and are effective at low concentrations.

Upon further study of the specification and appended claims, further objects and advantages of this invention will become apparent to those skilled in the art.

The invention thus relates to staining solutions containing dyes and stabilizers, especially staining solutions which contain thiazine dyes or mixtures of thiazine dyes with further dyes, which are characterized in that they contain, as the stabilizers, a combination of dimethylammonium sulfate and at least one crystallization inhibitor. Suitable crystallization inhibitors are preferably glycerol, polyethylene glycol, ethylene glycol and/or aliphatic ethers thereof, in particular ethylene glycol, glycerol or polyethylene glycol having a molecular weight of about 300. Such staining solutions, stabilized according to the invention, are used for staining biological materials in hematology, cytology and histology.

DETAILED DESCRIPTION

It has been found that especially the combination of dimethylammonium sulfate with ethylene glycol or glycerol or polyethylene glycol 200 reliably prevents precipitations of dye crystals. When polyethylene glycol 300 and aliphatic ethers of glycol, such as ethylene glycol monoethyl ether, ethylene glycol monoisopropyl ether, ethylene glycol monobutyl ether, ethylene glycol monomethyl ether or ethylene glycol dimethyl ether, were added, the solutions showed slight traces of precipitates in the temperature region around 9° C. but no detectable decrease in optical density after three months' storage. If the said crystalline inhibitors are added without dimethylammonium sulfate to the staining solutions, the formation of precipitates is delayed, but not prevented.

The proportion of the dimethylammonium sulfate stabilizer in the staining solution is generally 0.05 to 1.5% by weight, relative to the total solution, preferably 0.1 to 0.6% by weight and especially 0.2% by weight.

The proportion of the crystallization inhibitor is generally 1 to 15% by weight, relative to the total solution, preferably 3 to 5% and especially 3% by weight.

Comparative tests were carried out on the shelf life of the staining solutions according to the invention. For this purpose, samples of a freshly prepared May-Grunwald's eosin/methylene blue solution without dimethylammonium sulfate (DAS) and without crystallization inhibitor (CI), without DAS with CI, with DAS without CI and with 0.1% of DAS and 3% of various CI in each case were investigated. The decrease in staining performance at various storage temperatures was followed by measuring the optical density at 645 nm (thiazine component) and 523 nm (eosin). In addition, the quantity of precipitates was visually monitored.

It was found that, after a prolonged storage period at low temperatures, the staining solutions without ethylene glycol, glycerol or polyethylene glycol become completely useless, whereas the solutions with the stabilizer combination according to the invention still give good values after 32 weeks even below 9° C. As a result of the precipitation of dye crystals at low temperatures in solutions without the stabilizer combination according to the invention, the staining becomes not only weaker, but the staining pattern becomes more blue, since almost twice as much eosin precipitates than thiazine dye. After storage for 4 weeks at 9° C. or colder, solutions without an addition have an azure decrease of 29 to 39% and an eosin decrease of 46 to 60% and no longer stain adequately, whereas solutions with the stabilizer combination according to the invention were unchanged after 32 weeks' storage at 9° C. or colder.

According to the invention, novel stabilized staining solutions are available, which have a very long shelf life. These staining solutions stabilized according to the invention can be used for staining in, for example, hematology, cytology and histology. In the staining solutions of this invention, the amount of dye is fully conventional, e.g., typically in the range of 0.05-0.5 wt %, relative to the total solution. Of course, more generally, any amount of dye will be employable within the scope of this invention as long as it is effective to perform the staining intended by the solution. Similarly, any individual and relative amounts of the dimethylammonium sulfate and crystallization inhibitor components will be employable within the scope of this invention as long as, together, the two are effective for crystallization inhibition.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding German application P 37 36 490.1 (the priority document), are hereby incorporated by reference.

EXAMPLES

EXAMPLE 1

Preparation of a stabilized May-Grunwald's eosin/methylene blue solution 0.2 g of dimethylammonium sulfate is dissolved in a mixture of 97 ml of methanol and 3 ml of ethylene glycol, the solution is adjusted to a pH of 7.9, 0.12 g of May-Grunwald's eosin/methylene blue (MERCK) is added and the mixture is stirred for 3 hours. The solution is then filtered.

Whereas without ethylene glycol, in the temperature range from 9 to −25° C., precipitates already appear after 2 weeks and the optical density (645 nm/523 nm) rises from 1.62 to 2.63 after 8 weeks, it is constant at 1.62 utilizing the solutions of the present invention.

EXAMPLE 2

Preparation of a Leishman's eosin/methylene blue solution stabilized according to the invention 0.2 g of dimethylammonium sulfate is dissolved in a mixture of 97 ml of methanol and 3 ml of glycerol, the solution is adjusted to a pH of 7.9, 0.12 g of Leishman's eosin/methylene blue (MERCK) is added, the mixture is stirred for 18 hours and the solution is then filtered.

The optical density (625 nm/523 nm) of this solution is 1.34; as described above, with this solution, precipitates already appear after 2 weeks without stabilization; the optical density rises to 1.51 after 8 weeks.

EXAMPLE 3

Preparation of a staining solution with azure B and eosin 0.2 g of dimethylammonium sulfate is dissolved in a mixture of 97 ml of methanol and 3 ml of polyethylene glycol 200, the solution is adjusted to a pH Of 7.5, 0.1 g of azure B (MERCK) and 0.12 g of eosin (MERCK) are added and the mixture is stirred for 18 hours. The solution is then filtered.

Whereas without polyethylene glycol 200, in the temperature range from 9 to -25° C., precipitates already appear after two weeks and the optical density (637 nm/523 nm) rises without 8 weeks from 1.40 to 1.77, the optical density of the stabilized solution is constant at 1.40.

EXAMPLE 4

Preparation of a Wright's eosin/methylene blue solution 0.2 g of dimethylammonium sulfate is dissolved in a mixture of 97 ml of methanol and 3 ml of ethylene glycol monobutyl ether, the solution is adjusted to a pH of 7.7, 0.24 g of Wright's eosin/methylene blue (MERCK) is added and the mixture is stirred for 18 hours. The solution is then filtered.

Analogously to Example 3, precipitates appear after two weeks and the optical density (646 nm/523 nm) rises within 8 weeks from 1.68 to 2.0, whereas the optical density of the stabilized solution is 1.68 for the entire period.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A staining solution useful for biological material, comprising an effective staining amount of a thiazine or eosine dye or a mixture thereof, an effective stabilizing amount of dimethylammonium sulfate and a crystallization inhibiting amount of polyethylene glycol, ethylene glycol or an aliphatic ether thereof.

2. The staining solution of claim 1, wherein the crystallization inhibitor is ethylene glycol.

3. The staining solution of claim 1, wherein the crystallization inhibitor is polyethylene glycol of a molecular weight of about 200.

4. The staining solution of claim 1, wherein the crystallization inhibitor is ethylene glycol monobutyl ether.

5. The staining solution of claim 1, wherein the thiazine dye is methylene blue.

6. The staining solution of claim 1, wherein the dimethylammonium sulfate content is 0.05 to 1.5% by weight of the solution and the crystallization inhibitor content is 1 to 15% by weight of the solution.

7. The staining solution of claim 2, wherein the dimethylammonium sulfate content is 0.05 to 1.5% by weight of the solution and the crystallization inhibitor content is 1 to 15% by weight of the solution.

8. The staining solution of claim 5, wherein the dimethylammonium sulfate content is 0.05 to 1.5% by weight of the solution and the crystallization inhibitor content is 1 to 15% by weight of the solution.

9. A composition comprising an effective staining solution stabilizing amount of dimethylammonium sulfate and an amount of a compound effective to inhibit crystallization of a thiazine dye in a staining solution.

10. A method for staining cells in a hematological, cytological or-histological sample, comprising contacting the sample with an effective amount of the staining solution of claim 1.

11. A method for staining cells in a hematological, cytological or histological sample, comprising contacting the sample with an effective amount of the staining solution of claim 5.

12. A method for staining cells in a hematological, cytological or histological sample, comprising contacting the sample with an effective amount of the staining solution of claim 8.

* * * * *